United States Patent
Baym et al.

(10) Patent No.: US 9,468,932 B2
(45) Date of Patent: Oct. 18, 2016

(54) ACOUSTIC SOURCE FRAGMENTATION SYSTEM FOR BREAKING GROUND MATERIAL

(71) Applicant: Elwha LLC, Bellevue, WA (US)

(72) Inventors: Michael H. Baym, Cambridge, MA (US); Terry Briggs, Durham, NC (US); Robert Dunne, Highlands Ranch, CO (US); Clark J. Gilbert, Denver, CO (US); W. Daniel Hillis, Encino, CA (US); Roderick A. Hyde, Redmond, WA (US); Muriel Y. Ishikawa, Livermore, CA (US); Jordin T. Kare, Seattle, WA (US); Conor L. Myhrvold, Bellevue, WA (US); Nathan P. Myhrvold, Bellevue, WA (US); Tony S. Pan, Cambridge, MA (US); Clarence T. Tegreene, Bellevue, WA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 326 days.

(21) Appl. No.: 14/106,315

(22) Filed: Dec. 13, 2013

(65) Prior Publication Data
US 2015/0165445 A1    Jun. 18, 2015

(51) Int. Cl.
*B02C 19/18* (2006.01)
*A61B 17/225* (2006.01)

(52) U.S. Cl.
CPC .............. *B02C 19/18* (2013.01); *A61B 17/225* (2013.01)

(58) Field of Classification Search
CPC ....... B02C 19/18; G01S 5/30; G01S 5/0289; G01S 15/876
See application file for complete search history.

(56) References Cited

U.S. PATENT DOCUMENTS

| | | | |
|---|---|---|---|
| 4,646,756 A * | 3/1987 | Watmough et al. | 607/154 |
| 5,004,166 A * | 4/1991 | Sellar | 241/36 |
| 5,095,907 A * | 3/1992 | Kudo et al. | 600/439 |
| 6,156,549 A * | 12/2000 | Drewes et al. | 435/173.7 |
| 7,059,403 B2 | 6/2006 | Arnoldo Barrientos et al. | |
| 7,063,144 B2 | 6/2006 | Abramov et al. | |
| 7,213,681 B2 | 5/2007 | Birchak et al. | |
| 7,216,738 B2 | 5/2007 | Birchak et al. | |
| 7,804,741 B1 | 9/2010 | Snow et al. | |
| 7,813,223 B1 | 10/2010 | Snow et al. | |
| 2007/0295500 A1 | 12/2007 | Chuprakov et al. | |
| 2011/0011576 A1 | 1/2011 | Cavender et al. | |

OTHER PUBLICATIONS

Glenn Preminger, Gopal Badlani, Louis Kavoussi John Wiley & Sons, Nov. 29, 2011 p. 531.*
Glenn Preminger, Gopal Badlani, Louis Kavoussi John Wiley & Sons, Nov. 29, 2011 p. 546.*

* cited by examiner

*Primary Examiner* — Luke Ratcliffe
*Assistant Examiner* — Hovhannes Baghdasaryan
(74) *Attorney, Agent, or Firm* — Foley & Lardner LLP

(57) ABSTRACT

A system for fragmenting material includes an energy source, an acoustic transmitter, and a controller. The acoustic transmitter is coupled to the energy source and includes a unit acoustic source configured to emit an acoustic wave through a volume of ground material. The controller is coupled to the acoustic transmitter and is configured to engage the unit acoustic source such that the acoustic wave fractures the volume of ground material at a target location.

22 Claims, 8 Drawing Sheets

ACOUSTIC SOURCE FRAGMENTATION SYSTEM FOR BREAKING GROUND MATERIAL

BACKGROUND

Mining is the process of removing a desired in-ground material or mineral from a ground volume for further processing. Ground volumes include various materials such as overburden, ore (i.e. material including a mineral), caprock material, or still other types of material. Desirable materials may include precious metals, oil, gas, and other mined substances. Desirable materials located along a ground surface may be extracted from the ground volume without removing additional material (e.g., overburden, caprock material, etc.). However, desirable materials located below a ground surface may require operators to remove the additional material before extracting the desirable material.

Mining operations traditionally remove material using various methods. By way of example, a mining operation may utilize a blasting method to break free large amounts of material from the surrounding ground volume. However, blasting techniques may involve safety risks and may unintentionally break free additional material. Some mining operations employ cutting machines that work directly on an exposed rock face. However, these machines are comparatively slow and costly to operate and difficult to use in some circumstances. Other mining operations may utilize a rope saw to extract blocks of material from an above or belowground mine. Such a rope saw may include a plurality of sections having an embedded abrasive (e.g., diamond, etc.) that each remove a small amount of material as the section passes over the material. Operators may cycle the saw within pre-drilled holes cut laterally into the material and maintain tension on the rope saw to cut the material into blocks. However, the necessity of laterally pre-drilled holes may not allow rope saws to extract some configurations of subterranean material.

SUMMARY

One embodiment relates to a system for fragmenting material that includes an energy source, an acoustic transmitter, and a controller. The acoustic transmitter is coupled to the energy source and includes a unit acoustic source configured to emit an acoustic wave through a volume of ground material. The controller is coupled to the acoustic transmitter and is configured to engage the unit acoustic source such that the acoustic wave fractures the volume of ground material at a target location.

Another embodiment relates to a system for fragmenting material that includes an energy source, a first acoustic transmitter, a second acoustic transmitter, and a controller. The first acoustic transmitter is coupled to the energy source and includes a first unit acoustic source that is configured to emit a first acoustic wave through a volume of ground material. The second acoustic transmitter includes a second unit acoustic source that is configured to emit a second acoustic wave through the volume of ground material. The first acoustic transmitter and the second acoustic transmitter are arranged in a specified pattern. The controller is coupled to the first acoustic transmitter and the second acoustic transmitter. The controller is configured to engage the first unit acoustic source and the second unit acoustic source such that the first acoustic wave and the second acoustic wave additively fracture the volume of ground material at a target location.

Still another embodiment relates to a system for fragmenting material that includes an energy source, a first acoustic transmitter, a second acoustic transmitter, an acoustic receiver, and a controller. The first acoustic transmitter is coupled to the energy source and includes a first unit acoustic source that is configured to emit an acoustic wave through a volume of ground material. The second acoustic transmitter includes a second unit acoustic source that is configured to emit a test signal through the volume of ground material. The acoustic receiver is separated from the second acoustic transmitter by the volume of ground material and is configured to detect the test signal and provide an output signal. The controller is configured to: evaluate the test signal and the output signal to determine a characteristic of the volume of ground material; and engage the first unit acoustic source based on the characteristic of the volume of ground material such that the acoustic wave fractures the volume of ground material at a target location.

Yet another embodiment relates to a method for fragmenting material that includes providing an energy source, providing an acoustic transmitter including a unit acoustic source, identifying a target location within a volume of ground material, and engaging the unit acoustic source to fracture ground material at the target location with an acoustic wave.

The invention is capable of other embodiments and of being carried out in various ways. Alternative exemplary embodiments relate to other features and combinations of features as may be generally recited in the claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Acoustic source fragmentation systems are intended to provide an energy efficient and more precise alternative to traditional cutting, sawing, and blasting equipment. In some embodiments, acoustic source fragmentation systems utilize the inherently brittle properties of various materials to facilitate the fragmentation of the materials from a surrounding ground volume. Specifically, the systems may generate localized tension or shear forces within a material sufficient to break the material free. Further, acoustic source fragmentation systems may be controlled to reduce or eliminate the unintended fragmentation of material, which therefore improves the safety and efficiency of the extraction process.

Figure 1:
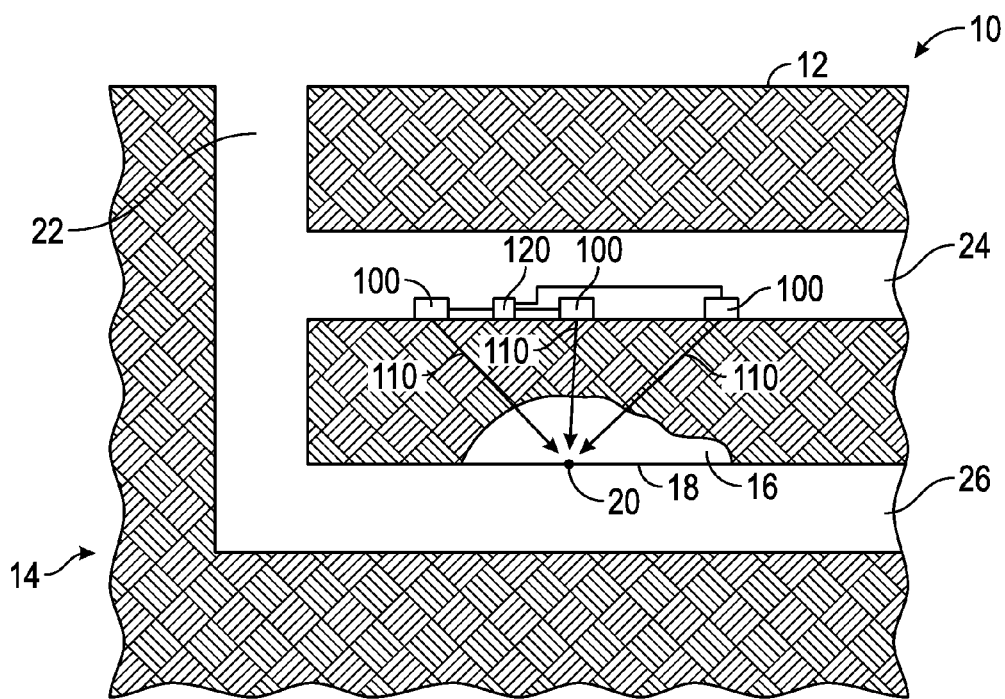
FIGS. 1-2 are side plan views of a mining operation including an acoustic fragmenting system, according to one embodiment.
Figure 2:
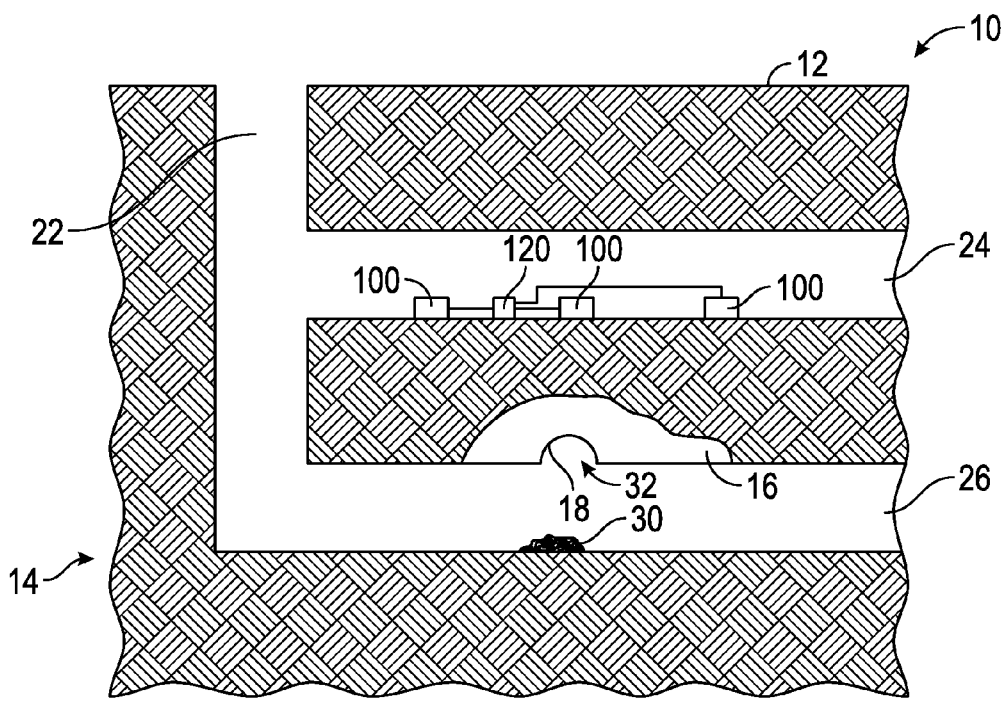

Referring to the exemplary embodiment shown in FIGS. 1-2, a mining operation 10 is configured to facilitate the removal of material from a portion of land. By way of example, such material may include ore, aggregate, oil (e.g., as part of a fracking process, etc.), gas, or other target substances. The disclosed fracturing technique may be used to facilitate extracting rock as part of a mining process or may be used for in-place fracturing (e.g., fracking, etc.). Such a portion of land may contain various features that are relevant to a mining operation or mining exploration (e.g., rock interfaces, fault lines, cavities, etc.). As shown in FIGS. 1-2, the portion of land includes a subterranean interface, shown as ground surface 12. According to an exemplary embodiment, ground surface 12 is a surface between air and a volume of subterranean material, shown as underground volume 14. According to an alternative embodiment, ground surface 12 may be the interface between another environment (e.g., water, space, etc.) and another underground volume (e.g., an oceanic surface, a lunar surface, etc.).

According to the embodiment shown in FIGS. 1-2, underground volume 14 includes a target material, shown as ore body 16. Ore body 16 may be a vein, a seam, or still another arrangement of material within underground volume 14. As shown in FIGS. 1-2, ore body 16 is a horizontal vein. In other embodiments, ore body 16 is otherwise disposed within underground volume 14 (e.g., a vertical vein, etc.).

Referring again to the embodiment shown in FIGS. 1-2, an underground mine is formed within underground volume 14. The underground mine facilitates the removal of a target material from underground volume 14. According to one embodiment, the underground mine includes a shaft 22, a first tunnel 24, and a second tunnel 26. In one embodiment, shaft 22 is vertical while tunnel 24 and tunnel 26 are horizontal. In another embodiment, at least one of shaft 22, tunnel 24, and tunnel 26 are angularly offset (e.g., relative to a vertical or horizontal reference, etc.). According to the embodiment shown in FIGS. 1-2, the underground mine includes one shaft and a pair of tunnels. According to various alternative embodiments, underground volume 14 includes a different arrangement of target materials, a plurality of target materials, or still other combinations of shafts 22 and tunnels 24. As shown in FIGS. 1-2, shaft 22 is spaced from ore body 16 while tunnel 24 and tunnel 26 are disposed along ore body 16. In other embodiments, at least one of shaft 22, tunnel 24, and tunnel 26 extend through a portion of ore body 16. In yet another embodiment, at least one of tunnel 24 and tunnel 26 are spaced from ore body 16. In still other embodiments, each of shaft 22, tunnel 24, and tunnel 26 are spaced from ore body 16.

According to one embodiment, an acoustic transmitter, shown as acoustic transmitter 100, is configured to emit an acoustic wave 110 through underground volume 14. In one embodiment, acoustic transmitter 100 includes a unit acoustic source configured to emit an acoustic wave through underground volume 14. In another embodiment, acoustic transmitter 100 includes a plurality of unit acoustic sources. The plurality of unit acoustic sources may be arranged in an array (e.g., a one dimensional, generally linear array, a two dimensional array, a three dimensional array) or otherwise distributed within acoustic transmitter 100. According to one embodiment, acoustic transmitter 100 includes unit acoustic sources that produce acoustic waves having the same or similar properties (e.g., frequency, amplitude, etc.).

According to another embodiment, the unit acoustic sources produce acoustic waves having different properties. By way of example, a first unit acoustic source may produce waves designed to impart tensile stresses on material at a target location and a second unit acoustic source may produce waves designed to impart shear stresses on material at the target location. This combination of tensile and shear stresses may improve the fragmentation rate (i.e. the period of time or energy required for spallation to occur) of the acoustic fragmentation system. In other embodiments, a first unit acoustic source and a second unit acoustic source emit acoustic waves designed to interact at the target location. According to one embodiment, the interaction includes aligning the phases of the waves at the target location such that the material at the target location experiences tensile stresses greater than those that would be imparted by a single acoustic wave. According to another embodiment, other types of interaction may occur between the acoustic waves at the target location.

In one embodiment, the unit acoustic sources are fixed within (i.e. cannot move relative to) acoustic transmitter 100 (e.g., coupled to a housing of acoustic transmitter 100) and configured to emit acoustic waves toward a target location. According to another embodiment, the unit acoustic sources are movably positioned within acoustic transmitter 100 (e.g., with a series of actuators, etc.) such that the acoustic waves may be steered toward a target location. According to still another embodiment, an electrical source induces magnetic fields within a ferromagnetic material of the unit acoustic sources to produce acoustic waves in a preferred direction (e.g., toward a target location). In one embodiment, the unit acoustic source is a line source. According to another embodiment, the unit acoustic source is another type of source (e.g., a point source, a curved source, a surface source, etc.). Varying the type of source may allow for acoustic transmitter 100 to emit waves in different directions (e.g., uniformly in all directions, waves focused on a particular area, etc.). According to another embodiment, acoustic transmitter 110 is positioned within underground volume 14 in an orientation that facilitates the propagation of acoustic waves 110 toward a target location. By way of example, acoustic transmitters 100 may be angled relative to a rock face, may be positioned within angled bore holes, or may be otherwise positioned to facilitate a preferred propagation direction. In still other embodiments, acoustic transmitters 100 are coupled to an actuator configured to move acoustic transmitters 100. Such an actuator may be engaged by a controller.

According to one embodiment, the various unit acoustic sources of acoustic transmitter 100 are controlled to emit waves simultaneously. In another embodiment, the various unit acoustic sources of acoustic transmitter 100 are controlled to emit waves successively (e.g., in a pattern, etc.). In embodiments where the various unit acoustic sources emit waves successively, acoustic transmitter 100 may include at least one delay circuit configured to delay a signal transmitted to each unit acoustic source. Such delay circuits may allow a control system to simultaneously send a single command signal to acoustic transmitter 100 while maintaining successive emission of waves from the various unit acoustic sources. In some embodiments, the delay circuits are physically coupled to the unit acoustic sources (e.g., with a wire). In another embodiment, the delay circuits may be coupled to the unit acoustic sources with a multiplexed circuit. In either embodiment, the delay circuits may reduce the computational or control load required of a controller.

As shown in FIGS. 1-2, three acoustic transmitters 100 are configured to emit acoustic waves 110 through underground volume 14. In other embodiments, more or fewer acoustic transmitters 100 are configured to emit acoustic waves 110 through underground volume 14. By way of example, tens or hundreds of acoustic transmitters 100 may be positioned to emit acoustic waves 110 through underground volume 14, thereby overcoming the strength of the rock at a target location without exceeding the strength of the rock at acoustic transmitters 100 or at a secondary maxima. According to the embodiment shown in FIGS. 1-2, acoustic transmitters 100 are positioned along a floor surface tunnel 24. In other embodiments, acoustic transmitters 100 are positioned along ground surface 12, along a surface of shaft 22, or along still another surface of the underground mine.

Referring still to the embodiment shown in FIGS. 1-2, acoustic transmitters 100 are configured to emit acoustic waves 110 toward a target location 20. As shown in FIG. 1, target location 20 is a point positioned on a work face 18. Work face 18 may be a surface of ore body 16 or another surface of the underground mine, according to various embodiments. As shown in FIG. 1, work face 18 is an overhead surface along the ceiling of tunnel 26. According to other embodiments, target location 20 is a two dimensional area positioned on work face 18. According to still other embodiments, target location 20 is offset from work face 18.

According to the embodiment shown in FIGS. 1-2, a controller 120 is coupled to acoustic transmitters 100. In one embodiment, controller 120 is coupled to each acoustic transmitter 100. In other embodiments, each acoustic transmitter 100 is coupled to a separate controller 120. Such separate controllers 120 may communicate with one another to engage acoustic transmitters 100 according to a coordinated control strategy. According to the embodiment shown in FIGS. 1-2, controller 120 is configured to engage acoustic transmitters 100 with a command signal such that acoustic waves 110 fracture a portion 30 of ore body 16 at target location 20. Controller 120 may consider various factors when determining the characteristics of the command signal sent to acoustic transmitters 100. By way of example, controller 120 may determine the potential signal that may be sent to one or more acoustic transmitters 100 using a predetermined maximum energy value (e.g., a maximum power value), various distances and angles between the acoustic transmitters, acoustic path delays between the acoustic transmitters, or still other characteristics.

As shown in FIG. 2, target location 20 is positioned along a ceiling of tunnel 26, and fractured portion 30 of ore body 16 falls to a floor of tunnel 26 to form a stope 32. In another embodiment, fractured portion 30 remains attached to ore body 16. Such material may be removed with a shovel, a drill, an explosive charge, or still another device to form stope 32. A new target location 20 may be selected, and additional ore body 16 may be fractured. Fractured portion 30 of ore body 16 may be removed from the underground mine for further processing (e.g., through a haulage level and a scram drift, etc.).

Figure 3:
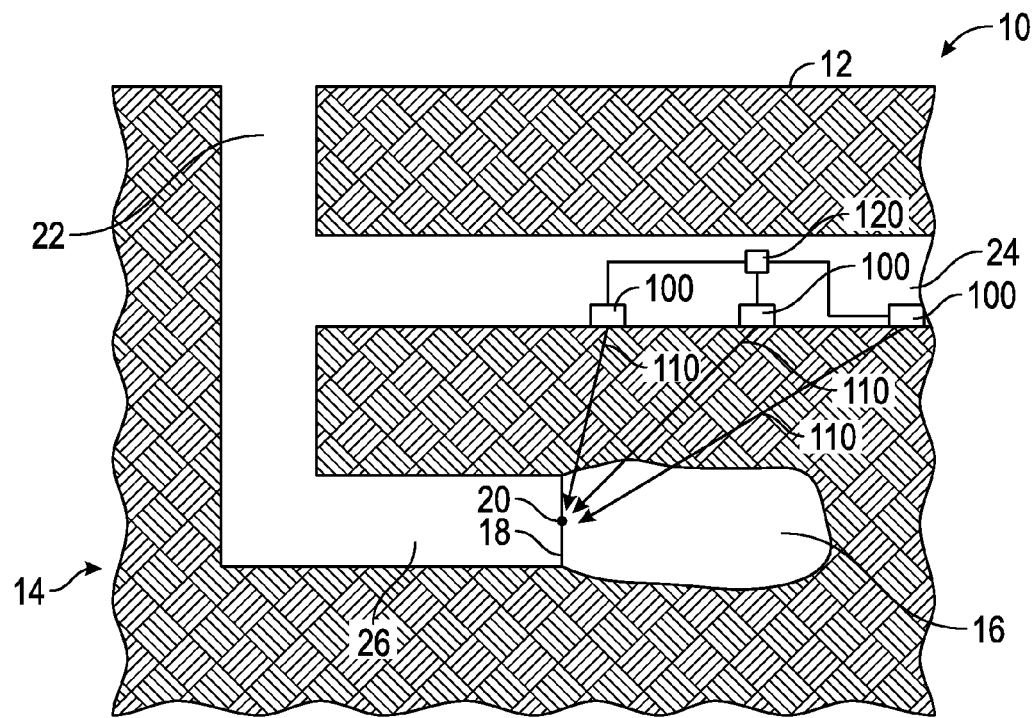
FIG. 3 is a side plan view of a mining operation including an acoustic fragmenting system, according to another embodiment.
Figure 4:
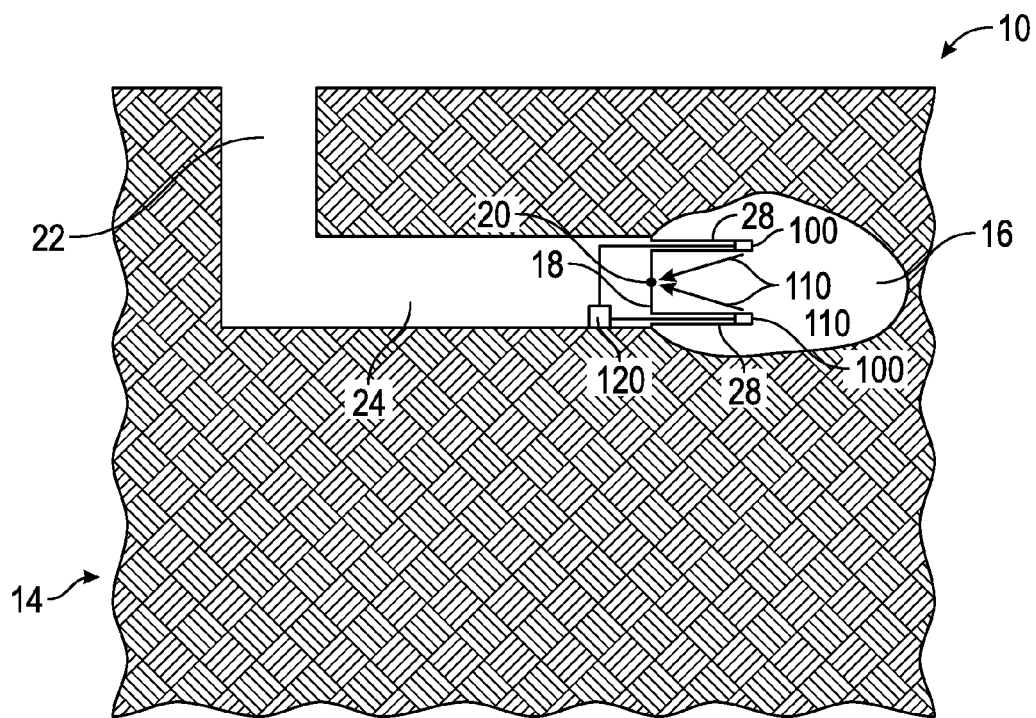
FIG. 4 is a side plan view of a mining operation including an acoustic fragmenting system, according to still another embodiment.

Referring next to the embodiments shown in FIGS. 3-4, acoustic transmitters 100 facilitate or engage in breast drilling. As shown in FIG. 3, work face 18 is positioned at an end of tunnel 26, and target location 20 is positioned on work face 18. Tunnel 24 extends further into underground volume 14 from shaft 22 than tunnel 26. According to the embodiment shown in FIG. 3, acoustic transmitters 100 are positioned along a floor surface of tunnel 24 in a location that is further into underground volume 14 than the end of tunnel 26. As shown in FIG. 3, controller 120 is configured to engage acoustic transmitters 100 to produce acoustic waves 110 directed toward target location 20. Acoustic waves 110 fracture a portion of ore body 16 to produce fractured target material and a stope. In one embodiment, the fractured material falls to a floor surface of tunnel 26 and is removed for further processing. In another embodiment, the fractured material remains attached to the remaining volume of ore body 16. Such fractured material may be removed with a shovel, a drill, an explosive charge, or still another device.

Figure 5:
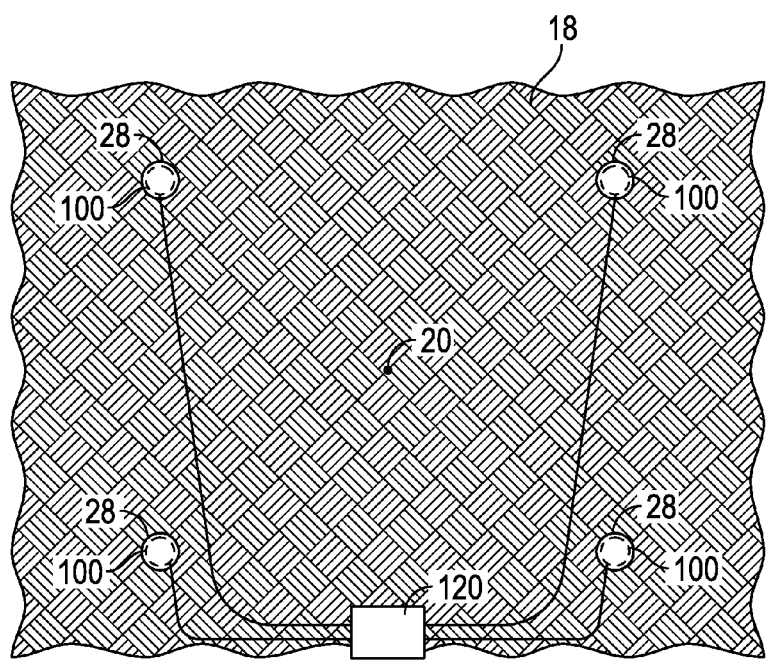
FIG. 5 is a front plan view of an acoustic fragmenting system placed in an end of a tunnel, according to one embodiment.

According to the embodiment shown in FIGS. 4-5, acoustic transmitters 100 are each positioned within a shaft 28 and located behind work face 18. In one embodiment, shafts 28 are drilled into an end (e.g., a breast face) of tunnel 24. In other embodiments, shafts 28 are otherwise formed in the end of tunnel 24. Work face 18 is the end of tunnel 24, and target location 20 is positioned on work face 18, according to one embodiment. As shown in FIG. 4, acoustic transmitters 100 are configured to emit acoustic waves 110 through underground volume 14 (e.g., through a portion of ore body 16) toward target location 20. According to one embodiment, controller 120 engages acoustic transmitters 100 to fracture a portion of ore body 16 to produce fractured target material and a stope. In one embodiment, the fractured material falls to a floor surface of tunnel 24 and is removed for further processing. In another embodiment, the fractured material remains attached to the remaining volume of ore body 16. Such fractured material may be removed with a shovel, a drill, an explosive charge, or still another device.

As shown in the end view of FIG. 5, a plurality of acoustic transmitters 100 are positioned within a plurality of shafts 28. Each shaft 28 may contain one or more transmitters 100 along its length. In one embodiment, the plurality of shafts 28 and acoustic transmitters 100 are arranged in a specified pattern. According to the embodiment shown in FIG. 5, the plurality of shafts 28 and acoustic transmitters 100 are arranged in a two-by-two rectangular array. In other embodiments, the plurality of shafts 28 and acoustic transmitters 100 are arranged in a rectangular array having different dimensions (e.g., three by two, etc.), a circular array, or a differently-shaped array. According to still another embodiment, the plurality of shafts 28 and acoustic transmitters 100 are irregularly arranged.

Figure 6:
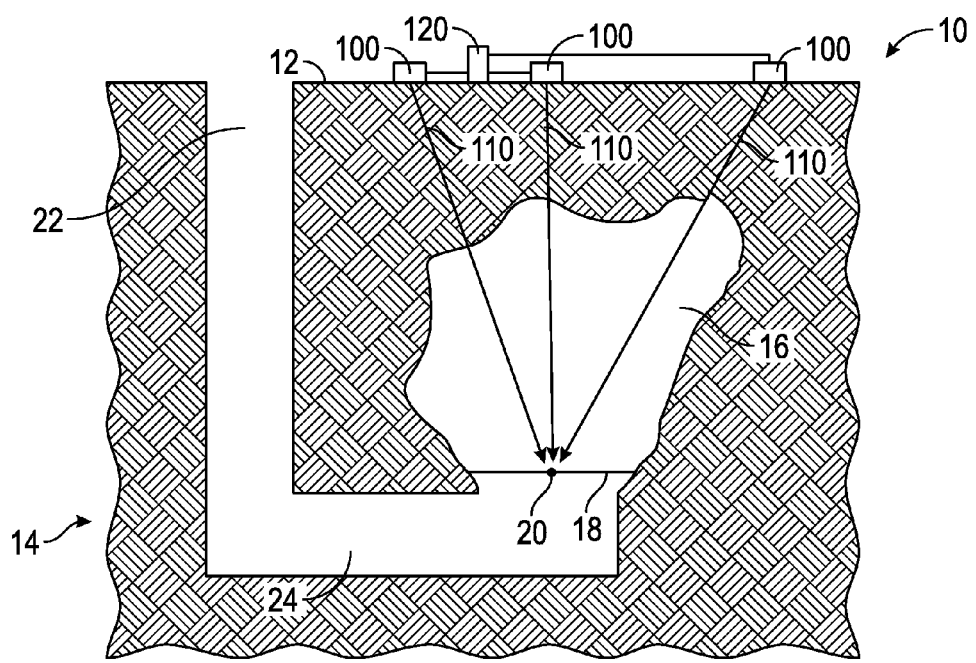
FIG. 6 is a side plan view of a mining operation including an acoustic fragmenting system, according to yet another embodiment.

Referring next to the embodiment shown in FIG. 6, the underground mine includes a shaft 22 and a tunnel 24 positioned to facilitate access to a lower portion of ore body 16. As shown in FIG. 6, ore body 16 is vertically oriented. According to the embodiment shown in FIG. 6, acoustic transmitters 100 are positioned at ground surface 12 and configured to emit acoustic waves 110 through underground volume 14 toward target location 20. In one embodiment, work face 18 is exposed to a portion of tunnel 24, and target location 20 is positioned on work face 18. As shown in FIG. 6, work face 18 is an overhead surface along the ceiling of tunnel 24. Controller 120 may engage acoustic transmitters 100 to fracture a portion of ore body 16 to produce fractured target material and a stope. In one embodiment, the fractured material falls to a floor surface of tunnel 24 and is removed for further processing. In another embodiment, the fractured material remains attached to the remaining volume of ore body 16. Such fractured material may be removed with a shovel, a drill, an explosive charge, or still another device.

Figure 7:
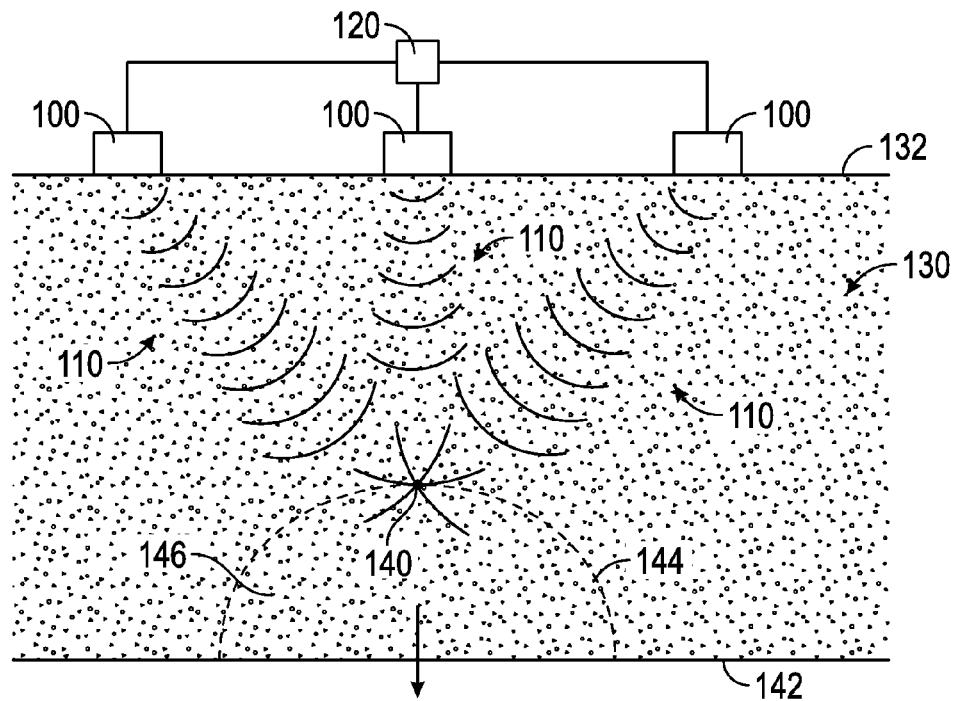
FIG. 7 is a cross sectional view of tensile or shear waves propagating through a rock body, according to one embodiment.
Figure 8:
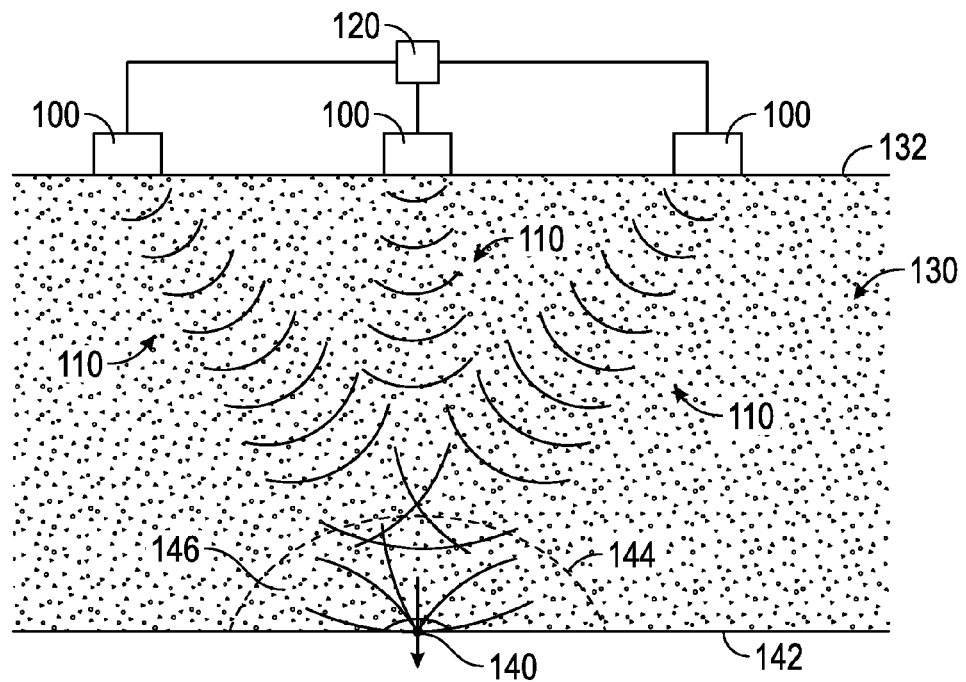
FIG. 8 is a cross sectional view of compressive waves propagating through a rock body, according to one embodiment.

According to the embodiment shown in FIGS. 7-8, acoustic waves 110 fracture a portion of underground volume 14 (e.g., a portion of ore body 16) by overcoming the strength of the material. By way of example, such strength may include the tensile strength, the shear strength, or the compressive strength of ore body 16. As shown in FIGS. 7-8, acoustic waves 110 overcome the strength of the material according to two operating modes. According to the first operating mode shown in FIG. 7, acoustic waves 110 include at least one of tensile and shear waves and facilitate bulk fracturing. According to the second operating mode shown in FIG. 8, acoustic waves 110 include compressive waves and facilitate surface spalling. Spalling is a process where fragments (i.e. flakes, pieces, spall, etc.) of material fracture from a ground volume due to internal stresses. Such spalling may occur at an exposed surface of a ground volume. Other fracturing modes are possible, including fracturing by compressive waves exceeding the compressive strength of the rock and fracturing by tensile waves produced by reflection of compressive waves from internal faults or density boundaries within the rock body, among others.

As shown in FIGS. 7-8, each acoustic transmitter 100 is coupled to a rock face 132 (e.g., a floor surface of a tunnel, a ceiling surface of a tunnel, a sidewall of a shaft within an end of a tunnel, a ground surface above an underground volume, etc.) of a rock body 130 (e.g., an ore body, another material, etc.). According to one embodiment, controller 120 engages acoustic transmitters 100 to emit acoustic waves 110 toward a target location 140. As shown in FIG. 7, target location 140 is spaced from a work face 142 (e.g., a work face of a target material or ore body, etc.). As shown in FIG. 8, target location 140 is positioned on work face 142.

According to the first mode of operation shown in FIG. 7, acoustic transmitters 100 direct at least one of tensile and shear acoustic waves 110 toward target location 140. Each acoustic wave 110 subjects the material within rock body 130 to tensile or shear stresses, respectively. In one embodiment, each individual acoustic wave 110 generates stresses that are less than the tensile or shear strength of the material within rock body 130. Different materials have different tensile strengths (e.g., 6 MPa for granite, 8 MPa for marble, 10 MPa for slate, etc.) and shear strengths (e.g., 12 MPa for granite, 14 MPa for marble, 25 MPa for slate, etc.). In one embodiment, the material of rock body 130 is marble having a tensile strength of 8 MPa, and each acoustic wave 110 generates a tensile stress of 3 MPa within the marble of rock body 130. Acoustic waves 110 from different acoustic transmitters 100 may combine at various positions between rock face 132 and work face 142. By way of example, two acoustic waves 110 may combine at a position between rock face 132 and target location 140, thereby generating a tensile stress of 6 MPa within the marble of rock body 130. Such additive tensile or shear stresses below the tensile strength or shear strength in the material do not fracture the material.

According to one embodiment, waves from acoustic transmitters 100 combine at target location 140 to generate a stress (e.g., a tensile stress, a shear stress) that is larger than the strength of rock body 130, thereby fracturing the volume of ground material. By way of example, each acoustic wave 110 may generate a tensile stress of 3 MPa within the marble of rock body 130. Three acoustic waves 110 from acoustic transmitters 100 may combine at target location 140 to generate a tensile stress of 9 MPa within the marble of rock body 130. This additive tensile stress causes fracture of the marble material, according to one embodiment. As shown in FIG. 7, target location 140 is positioned along a sweep path 144 that at least partially surrounds a target material 146. In one embodiment, fracture of the material at target location 140 releases target material 146. In another embodiment, acoustic waves 110 are directed toward a target location 140 that is successively moved along sweep path 144 to facilitate the bulk release of target material 146. In still another embodiment, acoustic waves 110 are directed toward a target location 140 that is successively moved within target material 146 to break up a volume of target material 146. Such an iterative process may be repeated until a substantial portion (e.g., 80%, 90%, etc.) of target material 146 is fragmented. According to another embodiment, controller 120 continuously engages acoustic transmitters 100 (i.e. acoustic transmitters 100 alternatively may continuously emit acoustic waves 110 while changing focus between various target locations 140). According to another embodiment, acoustic waves 110 include various components (e.g., a tensile component, a shear component, etc.) that combine to generate a larger stress on the material within rock body 130. According to still another embodiment, the material within rock body 130 is not homogeneous (e.g., contains existing fractures, contains various materials, etc.), which may facilitate fracture of the material below its tensile or shear strength.

In one embodiment, target location 140 is successively moved, and the new position for target location 140 is computed using a processing circuit. The processing circuit may facilitate the movement of target location 140 as a function of time. By way of example, target location 140 may be moved a distance of one meter every second. In other embodiments, target location 140 is moved based on information from one or more sensors (e.g., microphones, strain gauges, accelerometers, radar systems, etc.). The information may be related to whether the material at target location 140 has been fractured. By way of example, a sensor may provide sensor signals relating to the amount of energy transmitted past target location 140 or relating to a reflected acoustic wave. The sensor may be positioned at target location 140 and include a transmitter to communicate with a processor. In other embodiments, the sensor is positioned near acoustic transmitter 100. According to still another embodiment, target location 140 may be selectively positioned manually by an operator (e.g., using an operator input as part of a control system).

According to the second mode of operation shown in FIG. 8, acoustic transmitters 100 direct compressive acoustic waves 110 toward target location 140. Such compressive acoustic waves 110 propagate through the material within rock body 130 toward target location 140. Compressive acoustic waves 110 may be transmitted by rock having various imperfections. By way of example, compressive acoustic waves may be transmitted across crack faces within rock body 130, which may not transmit tensile or shear waves. According to one embodiment, the compressive acoustic waves 110 interface with work face 142 and reflect back toward acoustic transmitters 100 as reflected tensile waves 112. In one embodiment, the stresses generated by acoustic waves 110 and reflected tensile waves 112 are equal. In another embodiment, the stresses generated by reflected tensile waves 112 are less than the stresses generated by acoustic waves 110 (e.g., due to losses associated with the reflection off work face 142, etc.). As shown in FIG. 8, various reflected tensile waves 112 combine at target location 140 to overcome the tensile strength of the material within rock body 130. By way of example, the material within rock body 130 may be marble having a tensile strength of 8 MPa. Reflected tensile waves 112 may each generate a tensile stress of 3 MPa within the material of rock body 130. As shown in FIG. 8, three reflected tensile waves 112 combine at target location 140 to generate a tensile stress of 9 MPa within the material of rock body 130. In one embodiment, such a combination of reflected tensile waves 112 overcomes the tensile strength of the marble and spalls material at or near work face 142. In one embodiment, fracture of the material at target location 140 releases target material 146. In another embodiment, acoustic waves 110 are directed toward a target location 140 that is successively moved within target material 146 to spall material up to sweep path 144.

Figure 9:
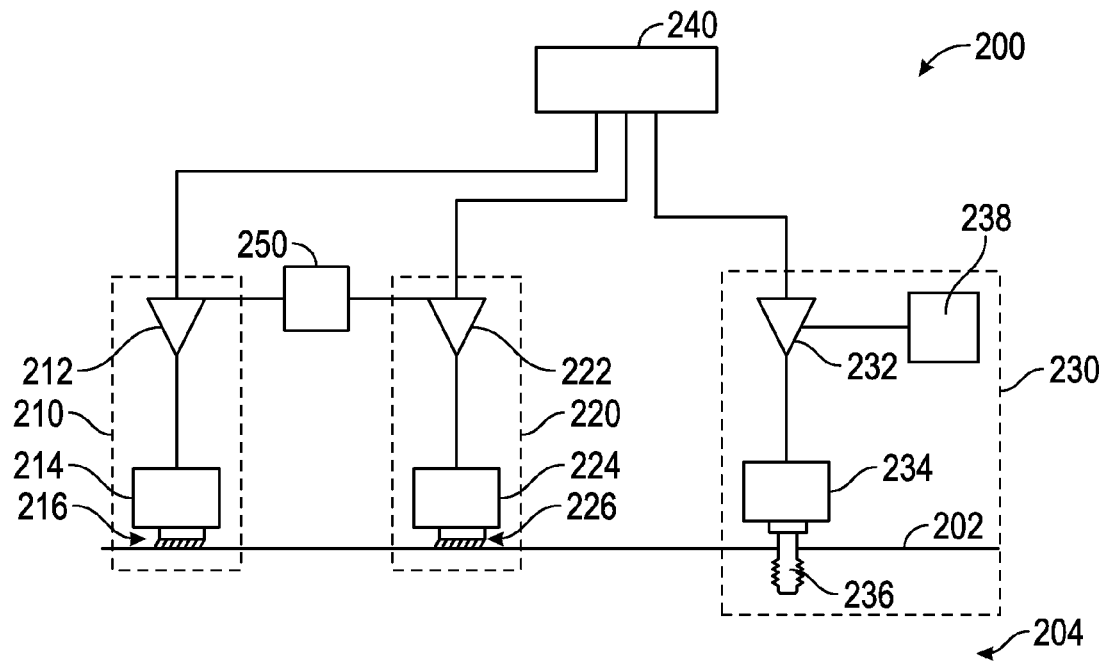
FIG. 9 is a schematic view of a system for fragmenting material including acoustic transmitters, according to one embodiment.

Referring next to the embodiment shown in FIG. 9, a system for fragmenting material, shown as system 200, includes a plurality of acoustic transmitters coupled to a rock face 202 of a rock body 204. As shown in FIG. 9, system 200 includes a first acoustic transmitter 210, a second acoustic transmitter 220, and a third acoustic transmitter 230. In other embodiments, system 200 includes only first acoustic transmitter 210, only third acoustic transmitter 230, only first acoustic transmitter 210 and third acoustic transmitter 230, or still another combination of acoustic transmitters. The transmitters may be arranged in a specified pattern to form an acoustic transmitter array (e.g., a rectangular array, a circular array, etc.) or may be otherwise positioned. According to the embodiment shown in FIG. 9, system 200 further includes a controller 240 that is coupled to first acoustic transmitter 210, second acoustic transmitter 220, and third acoustic transmitter 230. By way of example, controller 240 may be coupled to first acoustic transmitter 210, second acoustic transmitter 220, and third acoustic transmitter 230 with wired connections, with a wireless connection, with optical fibers, with a line-of-sight optical system, or with a pneumatic signal carrier, among other alternatives.

According to one embodiment, controller 240 sends signals (e.g., electrical signals) to first acoustic transmitter 210, second acoustic transmitter 220, and third acoustic transmitter 230. The acoustic transmitters thereafter emit waves (e.g., compressive, tensile, shear, etc.) having specified properties through rock body 204 toward a target location. The waves may not subject material positioned between the acoustic transceivers and the target location to fragmentation stresses (i.e. stresses in excess of the tensile strength, compressive strength, or shear strength of the material). However, according to one embodiment, the various waves from first acoustic transmitter 210, second acoustic transmitter 220, and third acoustic transmitter 230 act additively (i.e., cumulatively) the material at the target location, thereby exposing the material to fragmentation stresses. Such fragmentation stresses fragment (e.g., spalling, fracture, etc.) the material at the target location. In some embodiments, the characteristics of the acoustic waves are specified such that the material between acoustic transmitters and the target location also experiences fragmentation stresses.

As shown in FIG. 9, second acoustic transmitter 220, and third acoustic transmitter 230 include a driver 212, a driver 222, and a driver 232, respectively. In one embodiment, driver 212, driver 222, and driver 232 convert command signals from controller 240 into drive signals. By way of example, the drive signals may be one or more high power drive pulses. According to the embodiment shown in FIG. 9, driver 212, driver 222, and driver 232 provide the drive signals to a transducer 214, a transducer 224, and a transducer 234, respectively.

In some embodiments, at least one of driver 212, driver 222, and driver 232 receives electrical signals from controller 240 and sends a modified electrical signal to transducer 214, transducer 224, and transducer 234 (e.g., a magnetostrictive device, a voice coil, a piezoelectric device, etc.). According to one embodiment, the modified electrical signal includes characteristics that are specified by controller 240. Such characteristics may include, among others, wave form, frequency, amplitude, and phase. The modified electrical signal may have various shapes (e.g., square, sinusoidal, etc.) and may be pulsed or continuous. According to one embodiment, the characteristics of waves emitted by first acoustic transmitter 210, second acoustic transmitter 220, and third acoustic transmitter 230 correspond to those of the modified electrical signals received by transducer 214, transducer 224, and transducer 234 from driver 212, driver 222, and driver 232. The electric transducer 214 may be powered by an AC power line, a battery, or still another electrical energy source. In other embodiments, at least one of the acoustic transmitters is a pneumatic device or a thumper. By way of example, a controller may send a command signal to trigger actuation of the acoustic transmitter. Upon receiving the command signal, the pneumatic device may generate an acoustic wave (e.g., by driving a pneumatic actuator). A thumper may be configured to engage a trigger mechanism to initiate a detonation (e.g., an explosive charge, etc.) to drive a piston upon receiving the command signal from the controller.

In one embodiment, transducer 214, transducer 224, and transducer 234 convert the drive signals into acoustic impulses, which are emitted through rock body 204. As shown in FIG. 9, transducer 214 and transducer 224 are coupled to rock face 202 with a coupling medium 216 and a coupling medium 226, respectively. In one embodiment, coupling medium 216 and coupling medium 226 include cement. By way of example, coupling medium 216 and coupling medium 226 may facilitate the transmission of compressive acoustic waves. In other embodiments, coupling medium 226 is oil (e.g., to provide impedance matching). Transducer 234 is coupled to rock face 202 with a coupler 236. Coupler 236 facilitates the transmission of tensile or shear waves through rock body 204. In the embodiment shown in FIG. 9, coupler 236 is a bolted connection. In one embodiment, coupler 236 includes a bolt that is threaded directly into an aperture formed in rock body 204 (e.g., a drill hole). In another embodiment, coupler 236 includes a shaft coupled to rock body 204 (e.g., with an epoxy or adhesive).

Referring again to the embodiment shown in FIG. 9, first acoustic transmitter 210 and second acoustic transmitter 220 are coupled to a common energy source 250. By way of example, common energy source 250 may be an AC power line, a common battery, a common fuel tank, a common pressurized gas tank, or still another device. As shown in FIG. 9, third acoustic transmitter 230 includes a separate energy source 238. By way of example, separate energy source 238 may be an AC power line, a battery, a fuel tank, a pressurized gas tank, or still another device. In other embodiments, first acoustic transmitter 210 and second acoustic transmitter 220 each include a separate energy source.

In some embodiments, controller 240 facilitates the continuous flow of energy (e.g., electricity) from common energy source 250 and separate energy source 238. Such continuous flow may be required, for example, to produce a continuous acoustic wave from the acoustic transducers. In other embodiments, controller 240 is configured to intermittently allow energy (e.g., electricity) to flow from common energy source 250 and separate energy source 238 to the transducers. Such an intermittent flow may facilitate the transmission of a pulsed wave from the transducers.

Referring still to the embodiment shown in FIG. 9, controller 240 is configured to control first acoustic transmitter 210, second acoustic transmitter 220, and third acoustic transmitter 230 (e.g., by sending control signals, mechanically, etc.). In one embodiment, controller 240 is configured to engage first acoustic transmitter 210, second acoustic transmitter 220, and third acoustic transmitter 230 to fracture a volume of ground material. Controller 240 provides signals to first acoustic transmitter 210, second acoustic transmitter 220, and third acoustic transmitter 230 to produce acoustic waves having various characteristics. By way of example, such characteristics may include the timing (e.g., phase), amplitude, and wave form, among other features of the acoustic waves.

Figure 10A:
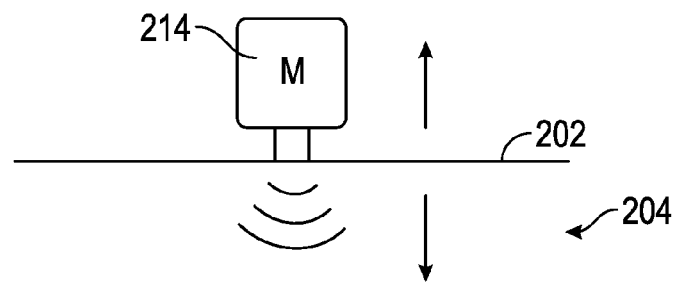
FIGS. 10A-10C are plan views of systems for attaching an acoustic transmitter to a rock body, according to various embodiments.
Figure 10B:
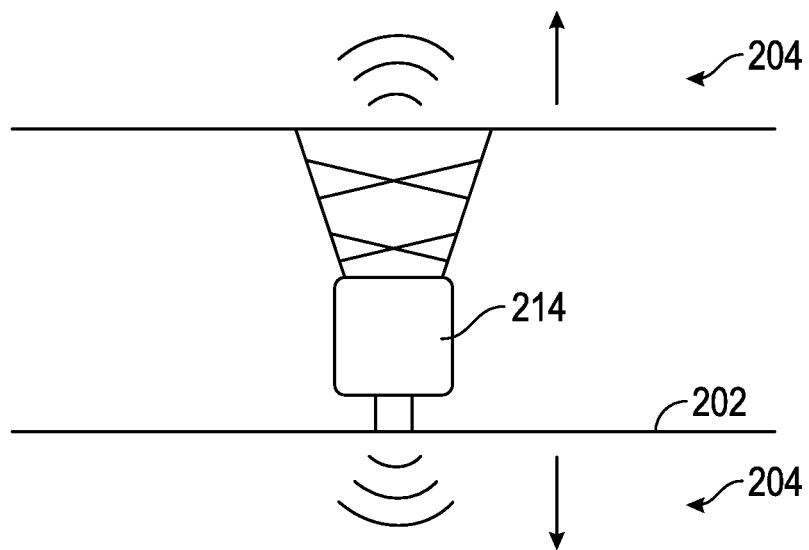
Figure 10C:
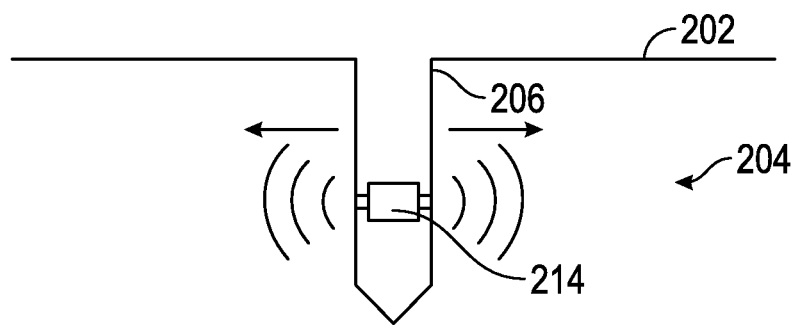

Referring next to FIGS. 10A-10C, transducer 214, transducer 224, or transducer 234 may be coupled to rock body 204 according to various techniques. As shown in FIG. 10A, transducer 214 is coupled to rock face 202 in a free arrangement. In the free arrangement, a portion of transducer 214 is coupled to rock face 202, and reaction forces from the operation of transducer 214 are opposed by the mass of transducer 214. In another embodiment, the reaction forces from the operation of transducer 214 are opposed by the mass of transducer 214 and a counterweight. As shown in FIG. 10B, transducer 214 is coupled to several rock surfaces with bracing 260. In one embodiment, bracing 260 extends downward and engages rock face 202 (e.g., with a bolted connection). In the embodiment shown in FIG. 10B, bracing 260 couples transducer to an opposing wall of a shaft, tunnel, or hole. Reaction forces from the operation of transducer 214 are transmitted by bracing 260 through the opposing wall and into rock body 204. As shown in FIG. 10C, transducer 214 is coupled (e.g., embedded, emplaced, etc.) within a shaft 206 (e.g., a drill hole). By way of example, transducer 214 may have a size larger than shaft 206, and transducer 214 may be driven into shaft 206. In another embodiment, transducer 214 is fixed within shaft 206 using a coupling material (e.g., cement, an adhesive, an epoxy, etc.).

Figure 11:
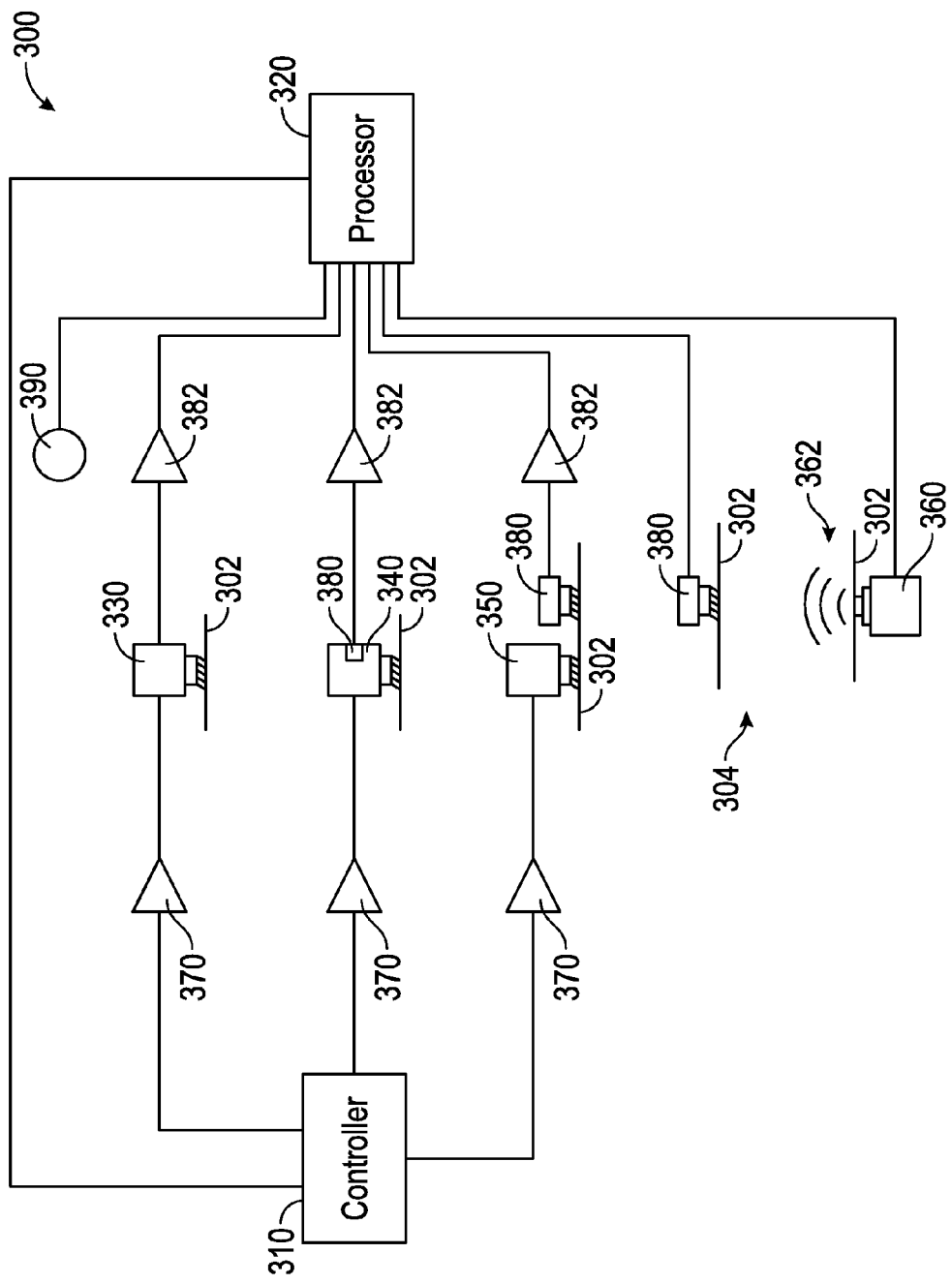
FIG. 11 is a schematic view of a system for fragmenting material including acoustic transmitters and acoustic receivers, according to one embodiment.

Referring next to the embodiment shown in FIG. 11, a system for fragmenting material, shown as system 300, is configured to accommodate the propagation characteristics of an underground volume. In one embodiment, system 300 characterizes the acoustic path between an acoustic transmitter and a target location using test signals and a bidirectional acoustic transmitter or acoustic receivers. Such characterization facilitates fracturing the material (e.g., by reducing the likelihood that acoustic waves from different acoustic transmitters will be out of phase at a target location). As shown in FIG. 11, system 300 includes a controller 310 coupled to a processor 320. Controller 310 may include processor 320, or they may be separate components. According to one embodiment, system 300 includes a bidirectional transducer 330 and a plurality of unidirectional transducers, shown as transducer 340, transducer 350, and transducer 360. Bidirectional transducer 330 both generates acoustic signals and functions as an acoustic receiver that receives test signals. As an acoustic receiver, incident acoustic waves are converted by bidirectional transducer 330 into a signal, which may be further conditioned or processed.

As shown in FIG. 11, a driver 370 is positioned between controller 310 and each of bidirectional transducer 330, transducer 340, and transducer 350. Controller 310 sends signals to drivers 370, which drive the transducers. In one embodiment, processor 320 evaluates signals from various components of system 300 to determine various characteristics of acoustic waves used to fracture material at a target location. By way of example, such characteristics may include the timing (e.g., phase), amplitude, and wave form, among other features of the acoustic waves. In one embodiment, processor 320 determines the characteristics by evaluating the time delay associated with acoustic waves 362 (e.g., the time required for an acoustic wave to travel from the transducers to the target location). In another embodiment, processor 320 determines the characteristics by evaluating the attenuation of rock body 304 (e.g., whether rock body 304 include void or other imperfections, etc.). In the embodiment shown in FIG. 11, controller 310 provides signals to drivers 370 to produce drive signals corresponding to the various characteristics. Bidirectional transducer 330, transducer 340, and transducer 350 thereafter generate acoustic waves having the various characteristics to fracture material at the target location.

According to one embodiment, transducer 360 is coupled to a rock surface 302 and generates a test signal, shown as acoustic wave 362, through rock body 304. In one embodiment, transducer 360 is coupled to rock surface 302 at or near a target location. Transducer 360 may be controlled by controller 310, processor 320, or may independently generate acoustic waves having known properties and timing. Acoustic wave 362 travels through rock body 304 and toward rock surfaces 302. Bidirectional transducer 330 receives acoustic wave 362 and provides a signal to processor 320, according to one embodiment. As shown in FIG. 11, acoustic wave 326 is also directed toward a plurality of acoustic receivers, shown as sensors 380. Sensors 380 may include microphones, strain gauges, accelerometers, piezoelectric devices, accelerometers, strain gauges, or still other devices. In the embodiment of FIG. 11, one sensor 380 is embedded within transducer 340, one sensor 380 is positioned alongside transducer 350, and one sensor 380 is independently positioned. Sensor 380 that is embedded within transducer 340 may share the same coupling to rock surface 302 as transducer 340. An additional sensor 390 is coupled to processor 320 and provides still other sensor information (e.g., the temperature of rock body 304). Processor 320 may receive still other inputs from still other systems (e.g., a conductivity system to provide water content, etc.). By way of example, processor 320 may receive signals (e.g., from a probe system) relating to the relative positions between transducer 360, sensors 380, bidirectional transducer 330, transducer 340, transducer 350. In other embodiments, system 300 may include still other arrangements of transducers and sensors (e.g., a single transducer and a plurality of sensors, sensors embedded or alongside each transducer, etc.).

As shown in FIG. 11, sensors 380 transmit sensor signals to processor 320. Such signals may engage signal modifiers 382 prior to passing on to processor 320. By way of example, signal modifiers 382 may include amplifiers, filters, signal conditioners, digitizers, or still other components. In other embodiments, the sensor signals are not modified before they are provided to processor 320.

In one embodiment, system 300 engages in conjugation whereby acoustic waves sent from the acoustic transmitters correspond with those received by acoustic receivers. By way of example, transducer 360 may send acoustic waves 362 having known properties from a target location. Various sensors 380 or bidirectional transducers 330 may receive acoustic waves 362 and convert the acoustic wave into a signal (e.g., an electric signal) that is provided to processor 320. Processor 320 may thereafter interface with controller 310 to provide command signals to drivers 370 such that acoustic waves are produced by bidirectional transducer 330, transducer 340, and transducer 350 to fracture the material at the target location. Such a process of sending a conjugated signal (e.g., an acoustic wave having characteristics that are similar to those of the acoustic wave received by sensors 380 or bidirectional transducer 330) may reduce the impact of variability within the intermediate rock body 304 on the ability of system 300 to fracture material at the target location. Further, sending a conjugated acoustic wave compensates for non-uniformities in the medium between bidirectional transducer 330, transducer 340, and transducer 350 and the target location.

In some embodiments, controller 310 utilizes the characterization information generated through sending test signals (e.g., test signals) in creating command signals for acoustic transmitters that are directed toward another target location (e.g., a target location that is below or above the previous target location). In other embodiments, system 300 relies only on conjugation and creates command signals by evaluating the properties of an acoustic wave generated by an acoustic transmitter for each target location.

According to one embodiment, acoustic wave 362 is sent by transducer 360 toward each of bidirectional transducer 330 and sensors 380. Each of bidirectional transducer 330 and sensors 380 may thereafter send a signal to processor 320. In embodiments where transducer 330 and sensors 380 are spaced relative to one another, the signal each sends to processor 320 may vary (e.g., have a different frequency, amplitude, phase angle, wave shape, etc.). These differences may be caused by, among other things, varying distances between transducer 360 and bidirectional transducer 330 and sensors 380, variations within the intermediate material between transducer 360 and bidirectional transducer 330, and conversion variations between the various bidirectional transducers 330 and sensors 380 (e.g., due to manufacturing variation, because the bidirectional transducers 330 and sensors 380 comprise different types of acoustic receivers, etc.). According to one embodiment, conjugation allows for each of bidirectional transducer 330, transducer 340, and transducer 350 to receive a conjugated command signal from controller 310. Such a conjugated signal may be tailored (i.e. specifically designed) for the location, type, and efficiency of each acoustic transmitter.

In another embodiment, at least one of bidirectional transducer 330, transducer 340, and transducer 350 are configured to generate a test signal (e.g., an acoustic wave) toward a sensor 380 positioned at a target location. Processor 320 may evaluate information relating to the test signal emitted by the transducer and sensor information from sensor 380 to characterize the intervening rock body 304. In one embodiment, processor 320 provides various signals to transducer 360 and engages in successive approximation or another iterative process until the signals received by sensor 380 has a preferred characteristic (e.g., have a preferred phase, a preferred amplitude, etc.). The preferred characteristic may be related to a preferred stress profile for rock body 304 at the target location. In one embodiment, the transducer is configured to first emit a low-power test signal and thereafter emit a high-power acoustic wave (e.g., a wave the produces stresses in the material greater than those produced by the low-power test signal) to fracture the material at the target location. By way of example, the high-power acoustic wave may have an amplitude that is greater than the amplitude of the low-power test signal. In another embodiment, various transducers are configured to individually emit test signals and thereafter emit acoustic waves to fracture the material at the target location.

In still another embodiment, least one of bidirectional transducer 330, transducer 340, and transducer 350 are configured to generate a test signal (e.g., a locating signal, an acoustic wave) toward a signal reflecting device as part of a probe system. In one embodiment, the signal reflecting device is positioned at a target location. In other embodiments, the signal reflecting device is otherwise positioned. In some embodiments, the signal reflecting device comprises a passive device configured to reflect incident acoustic waves. By way of example, such a passive device may include a metallic section attached to or embedded in the rock near the target area and having flat surfaces positioned perpendicular to incoming waves (e.g., to reflect waves back toward their originating point). In other embodiments, the passive device may include a cavity or cut in the rock having surfaces shaped to reflect incoming waves in a desired fashion (e.g., in a desired direction, etc.). In still other embodiments, the acoustic reflecting device is configured to receive and then retransmit waves. Such a signal reflecting device may include various systems that determine the angular position, amplitude, frequency, wave shape, or other characteristics of a test signal. Upon determining the characteristics of the test signal, the signal reflecting device may thereafter emit an outgoing wave. In one embodiment, the material around the target location may include defects, and the outgoing waves may be configured to reduce the risk that such material is not subjected to fracturing stresses. In other embodiments, the material at and around the target location includes a defect (e.g., one or more cracks, etc.). The outgoing waves from various transducers may combine and induce stresses that fracture the material at the target location without subjecting the surrounding material to fracturing stresses.

According to one embodiment, the outgoing wave includes the same characteristics as test signal as received by the signal reflecting device. In some embodiments, the test signal as received by the signal reflecting device may not be identical to the test signal as sent by the acoustic transmitter due to, for example, interaction with intermediate ground material. According to one embodiment, a bidirectional acoustic transmitter or an acoustic receiver thereafter receives the outgoing wave and sends an output signal to a processor. The processor may thereafter utilize the output signal when providing a command signal to an acoustic transmitter (e.g., to initiate an acoustic wave that fragments material). The signal reflecting device may also include an energy source (e.g., battery, generator, etc.) configured to power the transmission of the outgoing wave.

Such an acoustic fragmentation system having at least one of a passive and an active signal reflecting device may improve the efficiency or accuracy of the acoustic fragmentation system. By way of example, a wave sent through an intermediate ground volume once may not characterize the ground material as accurately as a wave sent through the intermediate ground volume twice. Accurate characterization of the ground material may occur where a test signal is sent from an acoustic transmitter and then retransmitted to a sensor positioned at the acoustic transmitter. Such accuracy may be important, for example, where a volume of ground material within or around the target location is intended to be left in place (i.e. not fragmented), and miscalculations may apply fragmentation waves to locations other than a target location (i.e. accidental mutual reinforcement of reflected or scattered acoustic waves or secondary maxima in the mutual interference pattern of waves from multiple acoustic sources may unintentionally fragment the preferably retained volume of ground material).

According to yet another alternative embodiment, the acoustic transmitters may send waves having specified characteristics to acoustic receivers positioned at other acoustic transmitters. In some embodiments, the specified characteristics include a frequency and a phase angle. By way of example, a controller may send a signal to an acoustic transmitter, which thereafter sends a wave toward a second acoustic transmitter. The second acoustic transmitter may then send a signal to a processor, thereby allowing the processor to determine the variation in a characteristic (e.g., phase angle). Such a variation may relate to a distance or an acoustic path delay between the acoustic transmitters. Using one of the various communication techniques discussed above, a processor may also determine the acoustic path delay between the acoustic transmitter and an acoustic receiver or signal reflecting device positioned at a target location within a target volume. In other embodiments, the intermediate ground volume is sufficiently characterized (e.g., using one of the methods discussed above) such that an acoustic transmitter may send an acoustic wave toward a target location (e.g., having a crack, interface, surface, etc.) and receive a reflected wave. The differences in various characteristics (e.g., phase angle, etc.) may allow for the determination of an acoustic path delay between the target location and the acoustic transmitter.

Figure 12A:
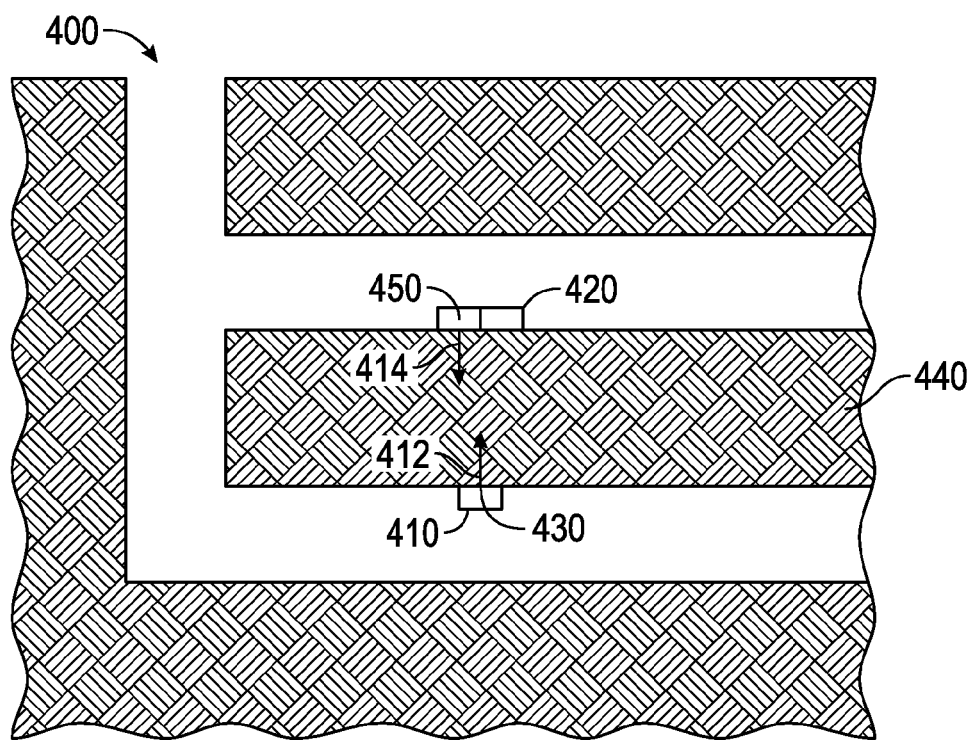
FIGS. 12A-12B are side plan views of a system for fragmenting material including acoustic transmitters and acoustic receivers, according to various embodiments.
Figure 12B:
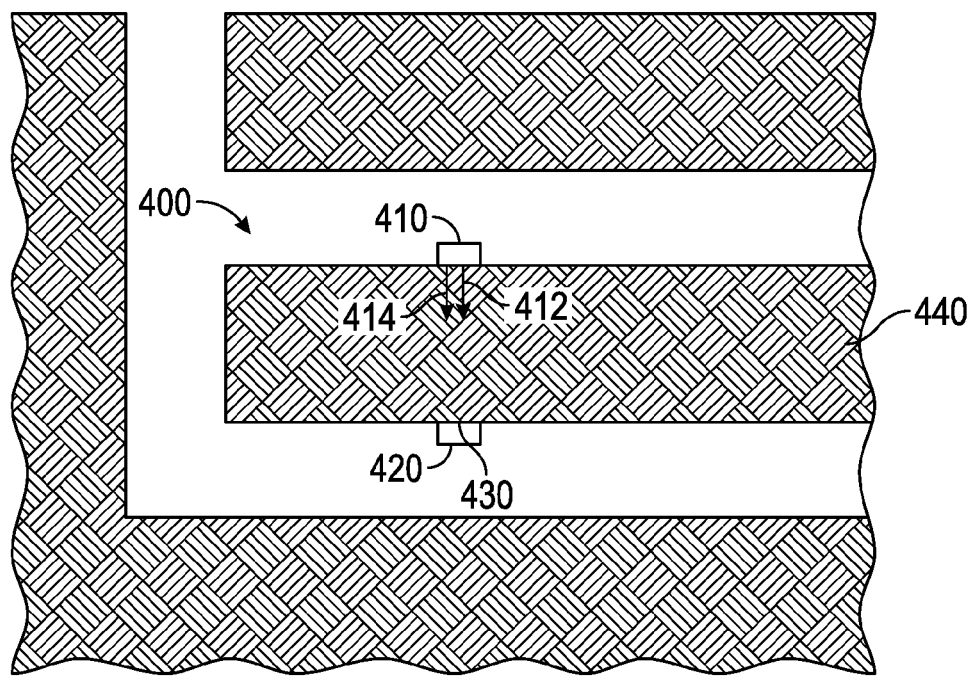

As shown in FIGS. 12A-12B, an acoustic fragmentation system 400 includes an acoustic transmitter 410 and an acoustic receiver 420. As shown in FIG. 12A, acoustic transmitter 410 is positioned at a target location 430. As shown in FIG. 12B, acoustic receiver 420 is positioned at target location 430. According to the embodiment shown in FIG. 12A, acoustic transmitter 410 is configured to emit a test signal 412 through an underground volume 440 toward acoustic receiver 420. In one embodiment, a controller evaluates test signal 412 and an output signal from acoustic receiver 420 to determine an acoustic path delay. The controller may use the acoustic path delay to engage a unit acoustic source of a second acoustic transmitter 450 such that an acoustic wave 414 fractures a volume of ground material at target location 430. According to the embodiment shown in FIG. 12B, acoustic transmitter 410 is configured to emit test signal 412 through underground volume 440 toward acoustic receiver 420. In one embodiment, a controller evaluates test signal 412 and an output signal from acoustic receiver 420 to determine an acoustic path delay. In the embodiment shown in FIG. 12B, the controller uses the acoustic path delay to engage a unit acoustic source of acoustic transmitter 410 such that an acoustic wave 414 fractures a volume of ground material at target location 430 (i.e. acoustic transmitter 410 may emit both test signal 412 and acoustic wave 414). In another embodiment, a controller may use the acoustic path delay to engage a unit acoustic source of a second acoustic transmitter such that acoustic wave 414 fractures a volume of ground material at target location 430.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the spirit of the appended claims.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed:

1. A system for fragmenting material, comprising:
an energy source;
a first acoustic transmitter coupled to the energy source and including a first unit acoustic source configured to emit a first acoustic wave through a volume of ground material;
a second acoustic transmitter including a second unit acoustic source configured to emit a second acoustic wave through the volume of ground material, wherein the first acoustic transmitter and the second acoustic transmitter are arranged in a specified pattern;
a controller coupled to the first acoustic transmitter and the second acoustic transmitter, wherein the controller is configured to engage the first unit acoustic source and the second unit acoustic source such that the first acoustic wave and the second acoustic wave additively fracture the volume of ground material at a target location; and
a probe system in communication with at least one of the first acoustic transmitter and the second acoustic transmitter, the probe system including a signal reflecting device, wherein the at least one of the first acoustic transmitter and the second acoustic transmitter is configured to emit an acoustic locating wave toward the signal reflecting device.

2. The system of claim 1, wherein the first acoustic wave and the second acoustic wave comprise tensile waves configured to subject the volume of ground material to tensile stresses.

3. The system of claim 1, wherein the first acoustic wave and the second acoustic wave comprise compressive waves configured to subject the volume of ground material to compressive stresses.

4. The system of claim 1, wherein the first acoustic wave and the second acoustic wave comprise shear waves configured to subject the volume of ground material to shear stresses.

5. The system of claim 1, wherein the at least one of the first acoustic transmitter and the second acoustic transmitter is configured to receive a reflected acoustic locating wave produced after the acoustic locating wave interacts with the signal reflecting device.

6. The system of claim 5, wherein the probe system includes a processing circuit configured to determine additional information about the volume of underground material.

7. The system of claim 6, wherein additional information includes an acoustic path delay between at least one of the first acoustic transmitter and the second acoustic transmitter and the signal reflecting device based on a feature of the acoustic locating wave and a feature of the reflected acoustic locating wave.

8. The system of claim 7, wherein the feature is a time difference.

9. A system for fragmenting material, comprising:
an energy source;
a first acoustic transmitter coupled to the energy source and including a first unit acoustic source configured to emit a first acoustic wave through a volume of ground material;
a second acoustic transmitter including a second unit acoustic source configured to emit a second acoustic wave through the volume of ground material, wherein the first acoustic transmitter and the second acoustic transmitter are arranged in a specified pattern;
a controller coupled to the first acoustic transmitter and the second acoustic transmitter, wherein the controller is configured to engage the first unit acoustic source and the second unit acoustic source such that the first acoustic wave and the second acoustic wave additively fracture the volume of ground material at a target location; and
an acoustic receiver, wherein the acoustic receiver is positioned at the target location.

10. The system of claim 9, wherein the first acoustic wave and the second acoustic wave comprise tensile waves configured to subject the volume of ground material to tensile stresses.

11. The system of claim 9, wherein the first acoustic wave and the second acoustic wave comprise compressive waves configured to subject the volume of ground material to compressive stresses.

12. The system of claim 9, wherein the first acoustic wave and the second acoustic wave comprise shear waves configured to subject the volume of ground material to shear stresses.

13. A system for fragmenting material, comprising:
an energy source;
a first acoustic transmitter coupled to the energy source and including a first unit acoustic source configured to emit an acoustic wave through a volume of ground material;
a second acoustic transmitter including a second unit acoustic source configured to emit a test signal through the volume of ground material;
an acoustic receiver separated from the second acoustic transmitter by the volume of ground material, wherein the acoustic receiver is configured to detect the test signal and provide an output signal; and
a controller configured to:
evaluate the test signal and the output signal to determine a characteristic of the volume of ground material by comparing a characteristic of the test signal with a characteristic of the output signal;

determine a propagation characteristic based on a feature of the test signal and the output signal, wherein the propagation characteristic includes at least one of the homogeneity, the sound propagation speed, the presence of defects, and the location of defects within the volume of ground material; and engage the first unit acoustic source based on the characteristic of the volume of ground material such that the acoustic wave fractures the volume of ground material at a target location.

14. The system of claim 13, wherein the acoustic receiver is configured to provide signals relating to at least one of the time of arrival, frequency, amplitude, and phase of the test signal.

15. The system of claim 13, wherein the characteristic is a time difference.

16. The system of claim 13, wherein the controller is configured to determine an acoustic path delay between the second unit acoustic source and the acoustic receiver.

17. The system of claim 16, wherein the characteristic is at least one of an activation timing, an amplitude, a wave type, a wave shape, a phase, and a frequency.

18. The system of claim 16, wherein the first acoustic transmitter is an electric device including a driver and an electric transducer.

19. The system of claim 18, wherein the activation signal includes at least one of an activation timing, an amplitude, a wave type, a wave shape, a phase, and a frequency.

20. The system of claim 19, wherein the controller is configured to determine a characteristic of the acoustic wave using a feature of the output signal.

21. The system of claim 20, wherein the characteristic and the feature are at least one of an activation timing, an amplitude, a wave type, a wave shape, a phase, and a frequency.

22. The system of claim 13, wherein the controller is configured to generate an activation signal for the first unit acoustic source using a characteristic of the output signal.

* * * * *